US00PP36155P3

(12) United States Plant Patent
Hoogkamp

(10) Patent No.: US PP36,155 P3
(45) Date of Patent: Sep. 24, 2024

(54) ***CURCUMA* PLANT NAMED 'CURSUMOK'**

(50) Latin Name: *Curcuma alismatifolia*
Varietal Denomination: Cursumok

(71) Applicant: NUBILUS B.V., Naaldwijk (NL)

(72) Inventor: Timothy Johan Herman Hoogkamp, Doetinchem (NL)

(73) Assignee: NUBILUS B.V., Naaldwijk (NL)

( * ) Notice: Subject to any disclaimer, the term of this patent is extended or adjusted under 35 U.S.C. 154(b) by 0 days.

(21) Appl. No.: 18/510,356

(22) Filed: Nov. 15, 2023

(65) Prior Publication Data

US 2024/0164232 P1 May 16, 2024

Related U.S. Application Data

(60) Provisional application No. 63/425,409, filed on Nov. 15, 2022.

(51) Int. Cl.
*A01H 5/02* (2018.01)
*A01H 6/00* (2018.01)

(52) U.S. Cl.
USPC ..... Plt./421
CPC ..... *A01H 6/00* (2018.05)

(58) Field of Classification Search
USPC ..... Plt./421
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Curcuma* plant named 'Cursumok', characterized by its upright plant habit with outwardly arching leaves; moderately vigorous to vigorous growth rate; freely clumping growth habit; medium to dark green-colored leaves with dark red-colored midvein; freely flowering habit; and large dense inflorescences with deep purplish red-colored upper flower bracts with dark red-colored apices positioned above the foliar plane on strong and erect peduncles.

2 Drawing Sheets

Figure 1:
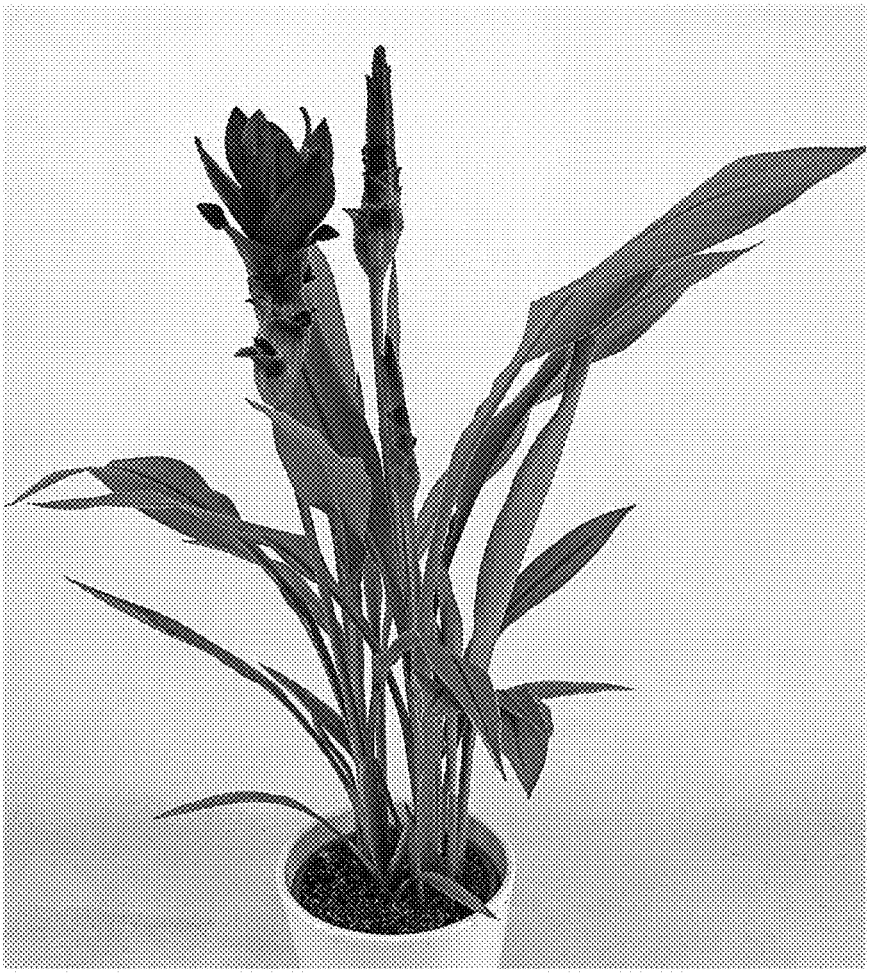

Botanical designation: *Curcuma alismatifolia.*
Cultivar denomination: 'CURSUMOK'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Nubilus B.V. of Naaldwijk, The Netherlands on Dec. 13, 2022, application number 2022/2922. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Curcuma* plant, botanically known as *Curcuma alismatifolia* and hereinafter referred to by the name 'Cursumok'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* plant originated from a cross-pollination made by the Inventor in June, 2013 in Naaldwijk, The Netherlands of a proprietary selection of *Curcuma alismatifolia* identified as code number 20102540-031, not patented, as the female, or seed, parent with a proprietary selection of *Curcuma alismatifolia* identified as code number 20092472-011, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands in July, 2016.

Asexual reproduction of the new *Curcuma* plant by axillary meristem culture in a controlled environment in Naaldwijk, The Netherlands since September, 2016 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cursumok'. These characteristics in combination distinguish 'Cursumok' as a new and distinct *Curcuma* plant:

1. Upright plant habit with outwardly arching leaves.
2. Moderately vigorous to vigorous growth rate.
3. Freely clumping growth habit.
4. Medium to dark green-colored leaves with dark red-colored midvein.
5. Freely flowering habit.
6. Large dense inflorescences with deep purplish red-colored upper flower bracts with dark red-colored apices positioned above the foliar plane on strong and erect peduncles.

Plants of the new *Curcuma* differ from plants of the female parent selection in the following characteristics:

1. Leaves of plants of the new *Curcuma* are darker green in color than plants of the female parent selection.
2. Plants of the new *Curcuma* have larger flowers than plants of the female parent selection.

Plants of the new *Curcuma* differ from plants of the male parent selection in the following characteristics:

1. Leaves of plants of the new *Curcuma* are darker green in color than plants of the male parent selection.
2. Flowers of plants of the new *Curcuma* have deep purplish red-colored upper flower bracts with dark red-colored apices whereas flowers of plants of the male parent selection have pink-colored upper flower bracts.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* are taller than plants of 'Curalimei'.
2. Flowers of plants of the new *Curcuma* have deep purplish red-colored upper flower bracts with dark red-colored apices whereas flowers of plants of 'Curalimei' have dark pink-colored upper flower bracts with dark red purple-colored apices.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet (FIG. 1) is a side perspective view of a typical plant of 'Cursumok' grown in a container.

Figure 2:
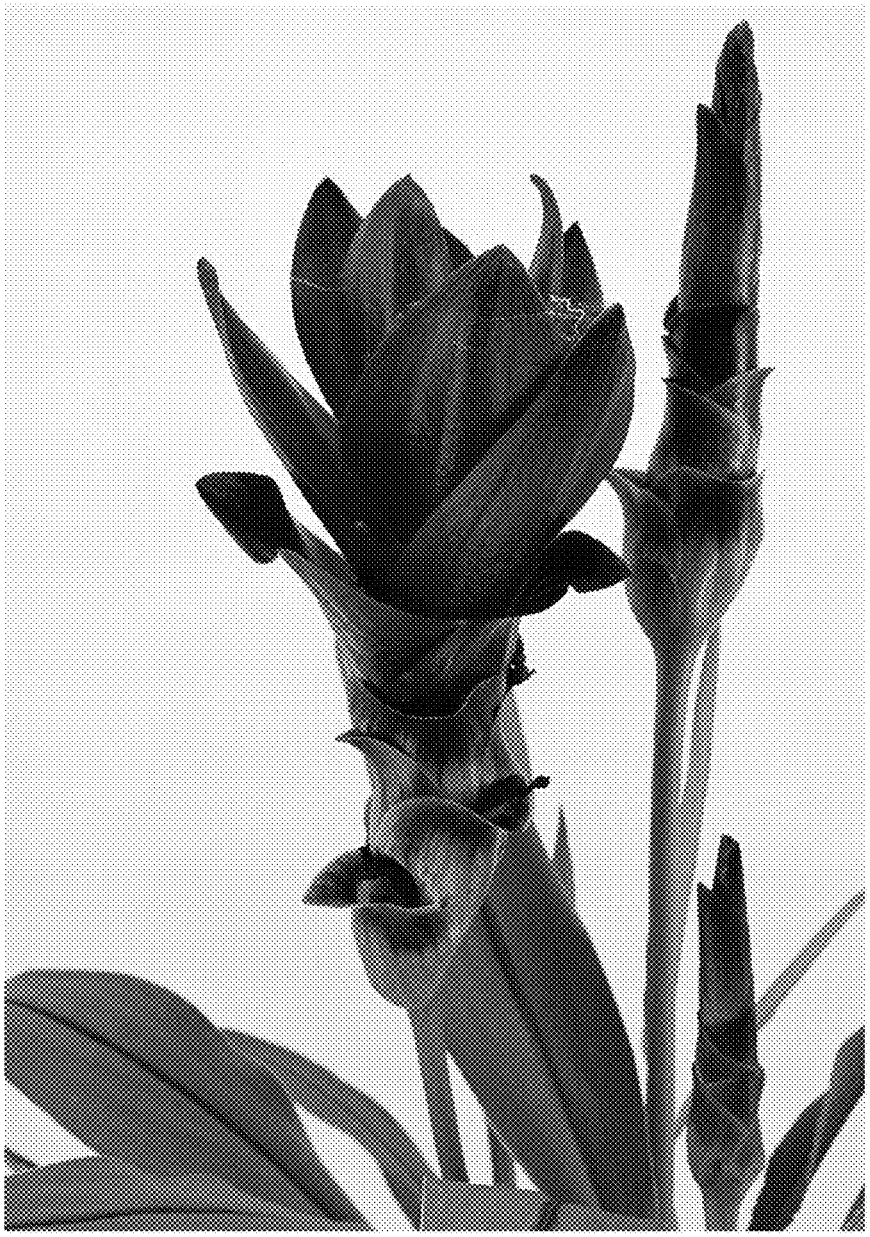

The photograph on the second sheet (FIG. 2) is a close-up view of a typical flowering plant of 'Cursumok'.

DETAILED BOTANICAL DESCRIPTION

The aforementioned photographs and following observations and measurements describe plants grown during the winter in 14-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 17 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Cursumok'.

Parentage:

*Female, or seed, parent*.—Proprietary selection of *Curcuma alismatifolia* code number 20102540-031.

*Male, or pollen, parent*.—Proprietary selection of *Curcuma alismatifolia* code number 20092472-011.

Propagation:

*Type*.—By axillary bud meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Upright plant habit with outwardly arching leaves; overall shape, broadly obovate; freely clumping habit with about eleven basal shoots forming per plant; moderately vigorous to vigorous growth habit and moderate growth rate.

*Plant height* (*soil level to top of foliar plane*).—About 50.8 cm.

*Plant height* (*soil level to top of floral plane*).—About 52.8 cm.

*Plant diameter*.—About 47.1 cm.

Leaf description:

*Leaf arrangement*.—Alternate; simple.

*Length, fully expanded*.—About 29.7 cm.

*Width, fully expanded*.—About 5.5 cm.

*Shape*.—Narrowly elliptic to lanceolate.

*Apex*.—Narrowly apiculate.

*Base*.—Attenuate, sheathing.

*Margin*.—Entire; not lobed and not undulate.

*Venation*.—Parallel.

*Aspect*.—Initially upright, then outwardly arching.

*Texture and luster, upper and lower surfaces*.—Smooth, glabrous; non-rugose; matte.

*Color*.—Developing leaves, upper surface: Close to between 143C and 144A; main vein, close to 176B. Developing leaves, lower surface: Close to between 143B and 144A to 144B; main vein, close to 138C. Fully expanded leaves, upper surface: Close to 137B; main vein, close to N186C; secondary veins, close to 137B. Fully expanded leaves, lower surface: Close to NN137D; main vein, close to 138C; secondary veins, close to NN137B.

*Leaf sheaths*.—Length: About 15.1 cm. Width: About 1 cm. Texture and luster, upper surface: Smooth, glabrous; glossy. Texture and luster, lower surface: Smooth, glabrous; slightly glossy. Color, upper surface: Close to 144A; towards the margins, close to 157D and mostly translucent; venation, close to 146B. Color, lower surface: Close to 144B; towards the margins, close to 157D and mostly translucent; venation, close to 143A.

*Petioles*.—Length: About 23.9 cm. Width: About 6 mm by 8 mm. Strength: Strong. Texture and luster, upper and lower surfaces: Smooth, glabrous; slightly glossy. Color, upper surface: Close to 137C; venation, close to NN137B. Color, lower surface: Close to 137B; venation, close to 137B.

Inflorescence description:

*Arrangement*.—Upright terminal spike inflorescences developing directly from the basal shoots with showy upper flower bracts; typically each spike with about eleven clusters each with about four flower; about 176 flowers buds and flowers developing per plant during the flowering season.

*Time to flower*.—In The Netherlands, plants flower from summer into autumn; flowering continuous during this period; plants begin flowering about twelve weeks after planting.

*Flower longevity*.—Flowers last about three days on the plant; flowers persistent; plants maintain good substance and appearance for about 40 days.

*Fragrance*.—Faint; somewhat spicy.

*Flower buds*.—Length: About 3.3 cm. Diameter: About 1 cm. Shape: Oblanceolate. Texture and luster: Smooth, glabrous; moderately glossy. Color: Proximally, close to 156D; distally, close to N82B.

*Inflorescence length*.—About 15.7 cm.

*Inflorescence diameter, with bracts*.—About 8.8 cm.

*Flowers*.—Diameter: About 1.9 cm by 2.6 cm. Depth: About 3.9 cm. Flower throat diameter: About 5 mm. Flower tube length: About 1.5 cm. Flower tube diameter: About 3.5 mm. Shape and arrangement: Zygomorphic with three petals, conspicuous labellum and two lateral corolla lobes (staminodia), fused towards the base; gamosepalous calyx with three sepals.

*Labellum*.—Length: About 2.5 cm. Width: About 1.9 cm. Shape: Obovate; fused towards the base. Apex: Emarginate. Margins: Entire; slightly undulate. Texture and luster, upper surface: Smooth, glabrous; slightly velvety; matte. Texture and luster, lower surface: Smooth, glabrous; slightly glossy. Color: When opening and fully opened, upper surface: Close to 83A fading towards the center and base to close to 83C; central narrow stripe, close to 17A; venation, similar to lamina colors; color does not change with subsequent development. When opening and fully opened, lower surface: Close to 83B fading towards the base to close to 83D; ventral band, close to 85A; venation, similar to lamina colors; color does not change with subsequent development.

*Lateral corolla lobes* (*staminodia*).—Length: About 2.2 cm. Width: About 9 mm. Shape: Ovate. Apex: Bluntly acute. Margins: Entire; not undulate. Texture and luster, upper surface: Smooth, glabrous; matte. Texture and luster, lower surface: Smooth, glabrous; slightly glossy. Color: When opening and fully opened, upper surface: Close to 155C and tinged towards the apex with close to 85B; venation, close to 85B and 85C; color does not change with subsequent development. When opening and fully opened, lower surface: Close to 155C and tinged towards the apex with close to 85B; venation, close to 85B and 85C; color does not change with subsequent development.

*Petals*.—Length, dorsal and lateral petals: About 1.8 cm. Width, dorsal petal: About 1.2 cm. Width, lateral petals: About 8 mm. Shape, dorsal petal: Oblong. Shape, lateral petals: Ovate. Apex, dorsal and lateral petals: Acute. Base, dorsal and lateral petals: Proximal 40% of the petal length is fused into a tube. Margins, dorsal and lateral petals: Entire; not undulate. Texture and luster, dorsal and lateral petals, upper surface: Smooth, glabrous; slightly glossy. Texture and luster, dorsal and lateral petals, lower surface: Smooth, glabrous; moderately glossy. Texture, throat and tube: Smooth, glabrous. Color, dorsal and lateral petals: When opening and fully opened, upper surface: Close to 85B and fading towards the base to close to 156D; venation, similar to lamina colors; color does not change with subsequent development. When opening and fully opened, lower surface: Close to 84A fading towards the base to close to 156D; venation, similar to lamina colors; color does not change with subsequent development. Color, flower throat: Close to NN155C; venation, close to NN155C. Color, flower tube: Close to N155A; venation, close to N155A.

*Calyx*.—Length: About 7 mm. Diameter: About 4 mm. Quantity of sepals and arrangement: Three in a single whorl; fused at the base. Sepal length: About 7 mm. Sepal width: About 4 mm. Sepal shape: Short oblong. Sepal apex: Broadly and bluntly acute. Sepal base: Broadly cuneate. Sepal margin: Entire. Sepal texture and luster, upper and lower surfaces: Smooth, glabrous; slightly glossy. Sepal color: When opening and fully opened, upper surface: Close to NN155D. When opening and fully opened, lower surface: Close to NN155D.

*Upper flower bracts*.—Quantity: About 13 upper bracts per inflorescence. Length: About 7.8 cm. Width: About 5 cm. Shape: Ovate; slightly concave. Apex: Acute. Base: Cuneate. Margin: Entire; not undulate. Texture and luster, upper and lower surfaces: Smooth, glabrous; glossy. Color: When opening and fully opened, upper surface: Close to 71A; towards the apex, close to 187A; venation, similar to lamina; color does not change with subsequent development. When opening and fully opened, lower surface: Close to 71A; towards the apex, close to 187A; venation, similar to lamina; color does not change with subsequent development.

*Lower flower bracts*.—Quantity: About six lower bracts per inflorescence. Length: About 4.1 cm. Width: About 4.7 cm. Shape: Broadly obovate to close to flabellate; strongly concave. Apex: Broadly and bluntly acute. Base: Cuneate. Margin: Entire; undulate. Texture and luster, upper surface: Smooth, glabrous; glossy. Texture and luster, lower surface: Smooth, glabrous; moderately glossy. Color: When opening and fully opened, upper surface: Close to 146D and towards the apex, close to N186D; venation, similar to lamina; color does not change with subsequent development. When opening and fully opened, lower surface: Close to 146B and towards the apex, strongly tinged with close to N186C and 187B; venation, close to 147A; color does not change with subsequent development.

*Peduncles*.—Length: About 46.1 cm. Diameter: About 7 mm. Strength: Strong. Aspect: Mostly erect. Texture and luster: Smooth, glabrous; matte. Color: Close to 143A to 143B.

*Stamens*.—Quantity: Two per flower; anthers fused. Filament length: About 1 cm. Filament diameter: About 4.5 mm. Filament color: Close to 85D and distally, close to 86A. Anther size: About 2 mm by 6 mm. Anther shape: Narrowly oblong. Anther color: Close to 85D. Pollen amount: Moderate. Pollen color: Close to 155A.

*Pistils*.—Quantity per flower: One. Pistil length: About 2.8 cm. Style length: About 2.5 cm. Style color: Close to NN155D. Stigma diameter: About 2 mm. Stigma shape: Cupped. Stigma color: Close to 155A. Ovary color: Close to 158A.

*Seeds and fruits*.—To date, seed and fruit development have not been observed on plants of the new *Curcuma*.

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Cursumok' as illustrated and described.

* * * * *